(12) United States Patent
Boden et al.

(10) Patent No.: US 7,584,901 B2
(45) Date of Patent: Sep. 8, 2009

(54) DISPENSING DEVICE FOR ACTIVE GELS

(75) Inventors: Richard Boden, Ocean, NJ (US); Craig Stumpf, Branchbury, NJ (US)

(73) Assignee: International Flavors & Fragrances, Inc., New York, NY (US)

( * ) Notice: Subject to any disclaimer, the term of this patent is extended or adjusted under 35 U.S.C. 154(b) by 921 days.

(21) Appl. No.: 10/738,323

(22) Filed: Dec. 16, 2003

(65) Prior Publication Data

US 2005/0127108 A1    Jun. 16, 2005

(51) Int. Cl.
*A24F 25/00* (2006.01)

(52) U.S. Cl. .............................. 239/60; 239/34; 239/44; 424/76.4

(58) Field of Classification Search ............... 239/44, 239/47, 60, 34; 424/76.1, 76.2, 76.3, 76.4; 43/131, 132.1; 428/905
See application file for complete search history.

(56) References Cited

U.S. PATENT DOCUMENTS

| | | | |
|---|---|---|---|
| 4,280,649 A | 7/1981 | Montealegre | |
| 4,306,679 A | 12/1981 | Dusek et al. | |
| 4,549,693 A | 10/1985 | Barlics | |
| 4,809,912 A * | 3/1989 | Santini | 239/60 |
| 5,081,104 A * | 1/1992 | Orson, Sr. | 239/44 |
| 5,857,620 A | 1/1999 | Nakoneczny | |
| 5,903,710 A * | 5/1999 | Wefler et al. | 239/47 |
| 5,909,845 A | 6/1999 | Greatbatch et al. | |
| 6,435,423 B2 | 8/2002 | Hurry et al. | |
| 6,553,712 B1 * | 4/2003 | Majerowski et al. | 43/131 |
| 6,969,024 B2 * | 11/2005 | He et al. | 428/905 |

FOREIGN PATENT DOCUMENTS

WO    WO 98/16262    4/1998

* cited by examiner

*Primary Examiner*—Steven J Ganey
(74) *Attorney, Agent, or Firm*—Licata & Tyrrell P.C.

(57) ABSTRACT

The present invention provides a dispensing device used for the slow controlled dispensing and diffusion of gels and thickened liquids. More particularly, the present invention relates to wick type air freshening devices, which employ a wick to convey materials from an enclosed container by capillary action.

6 Claims, No Drawings

DISPENSING DEVICE FOR ACTIVE GELS

FIELD OF THE INVENTION

The present invention provides a dispensing device used for the slow controlled dispensing and diffusion of gels, thickened liquids and vaporizable materials. More particularly, the present invention relates to wick type air freshening devices, which employ a wick to convey materials from an enclosed container by capillary action. The present invention prevents aspiration or swallowing of fragrances, and further prevents spills or leaks of the contents of the device.

BACKGROUND OF THE INVENTION

Liquid dispensers which employ a wick to convey a liquid or a volatile material from a container to an emanator are designed to slowly diffuse a liquid through a wick. The liquid may be a volatile scent-producing liquid, as in the case of air fresheners. In the case of wick type air fresheners, the scent-producing liquid is conveyed from a container, by means of capillary action through a wick, to an emanator, which diffuses the scent-producing liquid into the atmosphere in the form of a vapor, by the process of evaporation.

In order to be effective, the wick type dispensing device must provide the desired fragrance at a slow uniform rate, over an extended period of time. Prior art wick type air fresheners experience problems with poor flow of liquids and weight loss of fragrance, and health issues involving aspiration or swallowing of the fragrances.

The International Fragrance Association (IFRA) was created in 1973, primarily to take into account the vast quantity of safety information being generated by the Research Institute for Fragrance Materials (RIFM). IFRA took the safety data being generated by RIFM, and other data from different sources, and started to formulate guidelines for the safe use of fragrance ingredients where RIFM and others had identified potential hazards in their testing programs. IFRA Guidelines either ban or restrict ingredients in fragrance compounds and, therefore, in the final products, where safety testing had shown there to be a potential hazard of aspiration or swallowing.

U.S. Pat. No. 6,435,423 discloses a device for the diffusion of a volatile active ingredient with a hydrophobic medium, a volatile active ingredient and a superabsorbent substance. The superabsorbent substance is capable of forming a gel with the hydrophobic medium and is susceptible of enclosing the volatile active ingredient within the gel to permit diffusion of the volatile ingredient from the gel upon exposure to air. A wick is used to supply the gel with solvent so that the gel is continually moistened.

U.S. Pat. No. 4,549,693 discloses a dispenser, comprised of a two part circular housing, containing a round absorbent pad, whereby the effective aperture openings in the housing are controlled by an up and down sliding motion, bringing the apertures in each part, in and out of register.

U.S. Pat. No. 4,306,679 discloses a dispenser with a two part housing, containing a round absorbent pad, whereby the effective aperture openings in the housing are controlled by a twisting motion, bringing the apertures in each part, in and out of register.

U.S. Pat. No. 4,280,649 discloses an aperture control consisting of a two part rectangular carton, sliding up and down to provide a means to vary the aperture size.

All of the above patents describe a method to control the rate of diffusion of a scent-producing liquid into the atmosphere, by control of the aperture size in the air freshener container.

Wick in the bottle type of air freshener units have traditionally suffered from a lack of adequate control, to deliver a scent-producing liquid at a slow constant rate over an extended period of time. There remains a need for an improved dispensing device, capable of slow controlled dispensing and diffusion of fragrances and flavors which reduce aspiration or swallowing of the fragrance and further reduce spillage problems.

SUMMARY OF THE INVENTION

It is an object of the present invention to provide a dispensing device comprising an active gel; a reservoir which stores the active gel, and a wick which contacts the active gel on one end and conveys by capillary action said active gel at a slow substantially constant rate to the opposite end of said wick to diffuse the active gel into the ambient atmosphere by the process of evaporation. The active gel is a solid gel fragrance or a thickened fragrance.

DETAILED DESCRIPTION OF THE INVENTION

The present invention is an improved wick type dispensing device, useful for dispensing and diffusing vaporizable materials present in a thickened or gel form, at a slow controlled rate, over an extended period of time. The present invention is particularly suitable for applications requiring a slow uniform dispensing of a fragrance in a gel base. The key advantages of the present invention are that R-65 health issues such as aspiration and swallowing of fragrance are eliminated and the potential for spillage of the fragrance oil is greatly reduce as compared to traditional dispensers. In addition to other uses, the present invention can be used to dispense and diffuse active gels into the atmosphere, for example, as in air fresheners.

The present invention allows for a constant and slow controlled dispensing of a gel-based active material to a required location by a use of a wick. The absorbent wick conveys the active gel by capillary action, from a reservoir to another location for diffusion. The active gel is stored in a sealed reservoir which eliminates the need for venting and prevents spillage associated with liquid reservoir devices. The reservoir may be a bottle, a bag, a container or any other suitable structure.

In its simplest form, the dispensing device of the present invention comprises an active gel, a reservoir which stores the active gel; and a wick which contacts the active gel and conveys the active gel by capillary action to the top or opposite end of the wick at a slow substantially constant rate. The end or portion of the wick which is not in contact with the active gel may serve as an emanator by itself or may be in physical contact with an evaporative surface of an emanator which diffuses the active gel into the ambient atmosphere by the process of evaporation.

The wick is preferably polymeric or fibrous, although any other suitable materials may be used. Examples of suitable materials which may be used for the wick, include: cotton, cellulose fiber, carbon, synthetic polymeric fibers or foams felt, polyethylene, polypropylene, nylon, polyester, and porous ceramics. High density polyethylene and fibrous wicks composed of cellulose, polyester or nylon are preferred as they exhibit better flow and weight loss properties than other types of wicks, and further because they have a high porosity which is easier to fragrance. However, the wick may be made of any material capable of conveying a liquid or gel by capillary action. The wick may further be enclosed by an impermeable tubular element which is open at each end, if desired. The emanator is an absorbent material which provides a diffusing surface area. In one aspect of the invention the emanator may just be the end of the wick. One end of the wick protrudes into the reservoir, whereby the wick contacts the active gel and conveys the active gel by capillary action, to the other end of the wick in contact with the diffusing emanator. The wick inside the reservoir may be isolated from the active gel prior to use if desired by the use of a removable barrier.

The active gel is a thickened liquid or a solid gel. In one aspect, a solid polymer wick may be used for thickened fragrances In another aspect a fiber wick is used for solid gels. Solid gels are non-flowable, have a viscosity of greater than 1.5 cps.

In a preferred embodiment, the active gel is a mixture comprising an oil, fragrance, and thickeners. Thickeners include products such as Versagel, Cab-o-sil and Tween. The oil may be present in the mixture as a percent by weight range of about 90 to 99.8%. The fragrance may be present in the mixture as a percent by weight range of about 90 to 99.8%. The thickeners may be present in the mixture as a percent by weight range of about 0.1 to 10%. In a preferred embodiment the active gel is a mixture comprising about 95.97% fragrance, 4.0% Cab-o-sil and 0.03% Tween 20.

The reservoir container can be maintained remote from the emanator in desired embodiments for functional purposes. Further, the dispensing device may be contained in a housing such as a decorative package (i.e. themed package, multicolored package, etc.) or desired shape (i.e., football shape, Ballerina shape, flower shape, rectangle shape, triangle shape, letters, boat shape, etc.) for aesthetic purposes. The housing may comprise holes or vents to allow diffusion of the active gel to the atmosphere from the emanator.

The rate of diffusion of the active gel dispensing from the reservoir to emanator may be controlled by the type of the wick, the dimensions of the wick, the viscosity of the gel. The wick must be absorbent enough to maintain capillary action along its entire length. A smaller diameter long wick, will result in a slower gel dispensing rate, when compared to a larger diameter shorter wick. The length of time that a fragrance will last is dependant upon the type wick, the dimensions of the wick, the viscosity of the gel used. The fragrance in the present invention will last relatively longer than liquid type dispensers using the same wick and gel viscosity parameters. An impermeable tube may surround the wick to prevent active gel loss caused by lateral evaporation along the length of the wick.

In addition to use as a slow controlled gel dispenser suitable for use as an air freshener dispenser, the present invention can be used for any other purposes, i.e. insecticide dispenser, disinfectant dispenser. The active gel can be a fragrance, insect repellent, or possess other desired properties.

The emanator is preferably located on the end of the wick, opposite from the reservoir. Active gel refers to the material inside the reservoir and its content is dependent upon the intended use of the gel dispenser. An example of an active gels is a fragrance composition.

The reservoir may be constructed of plastic, glass, a flexible polymeric material, metal, or other suitable materials. The reservoir may be rigid or capable of collapsing inward in response to the reduced volume, as the active gel is depleted. The reservoir material must be impermeable and compatible with the active gel.

The wick may be part of a wick assembly comprising a wick and a holding mechanism which allows the wick to contact the active gel in the reservoir. The wick assembly extends in a continuous manner from the emanator, through to the reservoir, and in contact with the active gel contained within the reservoir. The end of the wick opposite the reservoir may act as an emanator alone, or it may contact an absorbent surface of a different desired emanator.

Barrier strips may be separated from the gel dispenser when it is ready for use. After removing the barrier strip, the active gel is free to contact the wick and travel by capillary action through the wick to the emanator.

In one embodiment, the wick is capped for air exclusion. The dispenser operation is then initiated by removing or rupturing the barrier between the wick and air.

In another one embodiment, the present invention may be said to comprise a sealed reservoir containing an active gel with a wick conveying the active gel to an emanator at a slow controlled rate, also including a barrier or means to maintain the active gel isolated from the wick prior to use.

In yet another embodiment the wick assembly may further comprise a wick housing element. The wick housing element encloses the wick, shields the active gel being conveyed and prevents lateral evaporation of the gel along the wick surface. The wick housing element may be comprised of plastic, ceramics, metals, polymeric material or metallic composite material depending on the desired properties, such as flexibility and compatibility with the active gel. The wick housing element may be of varying colors or designs as desired for the unit.

The emanator is the diffusing element of the gel dispenser. The emanator may be notched or otherwise formed to receive the wick. The overall form of the emanator is dependent upon its intended use. For example, the exposed end of the wick opposite the reservoir may serve the purpose of an emanator. In one aspect, the present invention can be used to deliver fragrance and/or disinfectant to a water supply, such as a toilet freshener. The emanator is absorbent so that it conveys and disperses the active gel into the atmosphere, by the process of evaporation. The emanator can be comprised of any absorbent material capable of conveying the active gel to a surface area to aid in its evaporation process. Some examples of suitable absorbent materials useful in an emanator are: felt, blotter paper, porous sponge, cellulose fibers, porous ceramics, and porous polymers. Additionally, the emanator may be fabricated in an aesthetically pleasing or functional shape, depending on cost or material restrictions.

Further, the emanator may include an impermeable covering on the outer side opposite the dispensing side, to prevent the evaporation losses. The wick sustains a sufficient quantity of active gel to continuously replenish the emanator over an extended period of time, as the emanator diffuses the active gel to a desired material.

What is claimed is:

1. A dispensing device comprising a reservoir for storing an active gel comprising an oil or fragrance present in the active gel at about 90 to 99.8 percent by weight; a wick with two ends wherein one end contacts the active gel and conveys by capillary action said active gel to the opposite end of the wick; and an emanator which is in physical contact with the end of the wick opposite the reservoir, wherein the emanator diffuses the active gel into the ambient atmosphere by the process of evaporation.

2. The dispensing device of claim 1 wherein the active gel is a solid gel fragrance or a thickened fragrance.

3. The dispensing device of claim 1 wherein the wick is polymeric.

4. The dispensing device of claim 1 wherein the wick is fibrous.

5. The dispensing device of claim 1 wherein the active gel is a mixture of about 95.97% fragrance, and about 4.0% thickener.

6. The dispensing device of claim 1 wherein the active gel is an insect repellent.

* * * * *